(12) United States Patent
Schwint et al.

(10) Patent No.: US 10,598,432 B2
(45) Date of Patent: Mar. 24, 2020

(54) PROCESS FOR THE PRODUCTION OF DILUTE ETHYLENE

(71) Applicant: LUMMUS TECHNOLOGY LLC, Bloomfield, NJ (US)

(72) Inventors: Kevin John Schwint, Bloomfield, NJ (US); Sanjeev Ram, Bloomfield, NJ (US)

(73) Assignee: LUMMUS TECHNOLOGY LLC, Bloomfield, NJ (US)

( * ) Notice: Subject to any disclaimer, the term of this patent is extended or adjusted under 35 U.S.C. 154(b) by 0 days.

(21) Appl. No.: 16/525,079

(22) Filed: Jul. 29, 2019

(65) Prior Publication Data

US 2019/0346202 A1 Nov. 14, 2019

Related U.S. Application Data

(62) Division of application No. 15/266,430, filed on Sep. 15, 2016, now Pat. No. 10,365,038.

(51) Int. Cl.
| | |
|---|---|
| *F25J 3/00* | (2006.01) |
| *F25J 3/02* | (2006.01) |
| *C07C 7/09* | (2006.01) |
| *C07C 7/00* | (2006.01) |

(52) U.S. Cl.
CPC ............ *F25J 3/0242* (2013.01); *C07C 7/005* (2013.01); *C07C 7/09* (2013.01); *F25J 3/0219* (2013.01); *F25J 3/0238* (2013.01); *F25J 2200/02* (2013.01); *F25J 2200/74* (2013.01); *F25J 2205/04* (2013.01); *F25J 2210/12* (2013.01); *F25J 2215/62* (2013.01); *F25J 2270/02* (2013.01); *F25J 2270/12* (2013.01); *F25J 2270/60* (2013.01); *F25J 2270/88* (2013.01)

(58) Field of Classification Search
CPC ........ C07C 11/04; F25J 3/0238; F25J 3/0242; F25J 2200/74; F25J 2205/04; F25J 1/0022; F25J 2270/88; F25J 1/0045; F25J 3/0209; F25J 3/0219
See application file for complete search history.

(56) References Cited

U.S. PATENT DOCUMENTS

| | | | | |
|---|---|---|---|---|
| 2,880,592 | A * | 4/1959 | Cobb, Jr. ................. | C07C 7/04 62/621 |
| 4,167,402 | A * | 9/1979 | Davis ..................... | C07C 7/005 62/630 |
| 6,116,050 | A * | 9/2000 | Yao ........................ | F25J 3/0209 62/630 |
| 6,631,626 | B1 * | 10/2003 | Hahn ..................... | B01D 53/04 62/612 |
| 6,662,589 | B1 * | 12/2003 | Roberts ................. | F25J 1/0241 62/425 |
| 2002/0157538 | A1 * | 10/2002 | Foglietta ............... | F25J 3/0209 95/237 |
| 2013/0102827 | A1 * | 4/2013 | Simon ................... | C10G 70/04 585/809 |

* cited by examiner

*Primary Examiner* — Keith M Raymond
(74) *Attorney, Agent, or Firm* — Osha Liang LLP

(57) ABSTRACT

Processes and systems for recovery of a dilute ethylene stream are illustrated and described. More specifically, embodiments disclosed herein relate to processes and systems for separation of a dilute ethylene stream from an offgas or other vapor streams, where the ultra-low temperature refrigeration for the desired separations is provided by the offgas itself, and only moderately-low temperature externally supplied propylene refrigerants (for example, at −40° C. to 15° C.) are necessary.

9 Claims, 1 Drawing Sheet

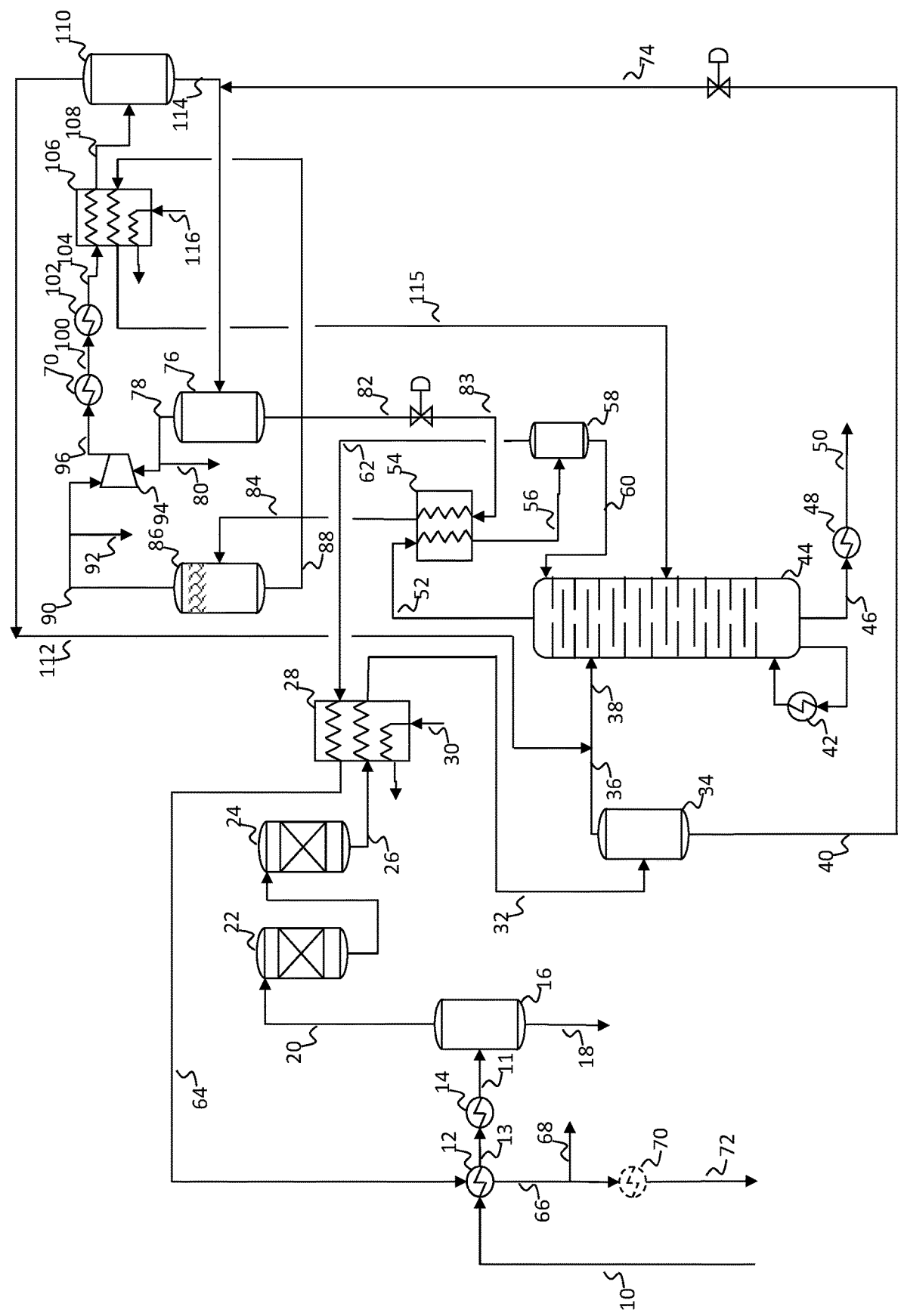

PROCESS FOR THE PRODUCTION OF DILUTE ETHYLENE

FIELD OF THE DISCLOSURE

Embodiments disclosed herein relate generally to systems and processes for recovery of a dilute ethylene stream.

BACKGROUND

Refinery offgases, such as offgases from fluid catalytic cracker units and coker units, often contain olefins, such as ethylene, which can be recovered and used in various processes. These refinery offgases often contain a mixture of gases, which may include hydrogen, methane, ethane, ethylene, and propylene, among other lighter and heavier components.

Various processes have been proposed to recover ethylene from such a mixture of gases. For example, U.S. Pat. Nos. 6,705,113, 5,979,177, 5,502,971, and U.S. Pat. No. 3,765,435 each relate to methods for recovering olefins from gas mixtures.

Many of these processes require ultra-low temperature refrigerant (for example, at or below −70° C.) and use methane refrigeration, or refrigeration systems that require high-purity ethylene and high purity propylene refrigerant systems, or binary refrigerant systems utilizing ethylene and propylene. Unfortunately, these high-purity streams are not always readily available on-site, and alternatives to such external refrigeration systems are needed.

SUMMARY OF THE CLAIMED EMBODIMENTS

Embodiments herein are directed toward systems and processes for the production of a dilute ethylene feedstock by separation of $C_3$s and heavier components from the offgas of a fluid catalytic cracker (FCC), residue fluid catalytic cracker (RFCC), or a vacuum gas oil (VGO) cracking unit, among other various sources. Such separations may be achieved according to embodiments herein without the need for an externally supplied ultra-low temperature (methane, ethane, or ethylene) refrigerant or binary refrigerant.

In one aspect, embodiments disclosed herein relate to a process for producing a dilute ethylene stream. The process may include cooling and partially condensing a feedstock comprising hydrogen, methane, ethane, ethylene, and $C_{3+}$ hydrocarbons. The cooled and partially condensed feedstock may be separated into a vapor feed stream and a liquid feed stream, where the liquid feed stream comprises a portion of the ethylene contained in the feedstock. The vapor feed stream may be separated in a deethanizer to recover an overhead stream and a bottoms product stream comprising the $C_{3+}$ hydrocarbons. The liquid feed stream may be separated into a first vapor fraction and a first liquid fraction. The overhead stream may be cooled and partially condensed via indirect heat exchange with a refrigerant comprising at least a portion of the first liquid fraction.

In another aspect, embodiments disclosed herein relate to a system for producing a dilute ethylene stream. The system may include a deethanizer feed chiller for cooling and partially condensing a feedstock comprising hydrogen, methane, ethane, ethylene, and $C_{3+}$ hydrocarbons. A deethanizer feed separator may be provided for separating the cooled and partially condensed feedstock into a vapor feed stream and a liquid feed stream, wherein the liquid feed stream comprises a portion of the ethylene contained in the feedstock. A deethanizer is used for separating the vapor feed stream to recover an overhead stream and a bottoms product stream comprising the $C_{3+}$ hydrocarbons. A refrigerant drum may separate the liquid feed stream into a first vapor fraction and a first liquid fraction. Also provided may be a deethanizer overhead condenser for cooling and partially condensing the overhead stream via indirect heat exchange with a refrigerant comprising the first liquid fraction.

In another aspect, embodiments disclosed herein relate to a process for producing a dilute ethylene stream. The process may include cooling and partially condensing a feedstock comprising hydrogen, methane, ethane, ethylene, and $C_{3+}$ hydrocarbons, and separating the cooled and partially condensed feedstock into a vapor feed stream and a liquid feed stream. The liquid feed stream contains a portion of the ethylene contained in the feedstock. The vapor feed stream may then be separated in a deethanizer to recover an overhead stream and a bottoms product stream comprising the $C_{3+}$ hydrocarbons, and the liquid feed stream may be separated into a first vapor fraction and a first liquid fraction, used for cooling and partially condensing the overhead stream via indirect heat exchange with the first liquid fraction, forming a warmed first liquid fraction. The cooled and partially condensed overhead stream may be separated into a liquid reflux stream and an overhead vapor dilute ethylene product stream. The warmed first liquid fraction may be separated into a second vapor fraction and a second liquid fraction. The first vapor fraction and the second vapor fraction may be compressed to form a compressed refrigerant stream, which may be cooled via indirect heat exchange with the second liquid fraction. The second liquid fraction may then be fed to the deethanizer. The cooled compressed refrigerant stream may be separated into a third vapor fraction and a third liquid fraction, the third vapor fraction being fed to the deethanizer; and the third liquid fraction being combined with the liquid feed stream.

In another aspect, embodiments disclosed herein relate to a system for producing a dilute ethylene stream. The system may include a deethanizer feed chiller for cooling and partially condensing a feedstock comprising hydrogen, methane, ethane, ethylene, and $C_{3+}$ hydrocarbons, and a deethanizer feed separator for separating the cooled and partially condensed feedstock into a vapor feed stream and a liquid feed stream. The liquid feed stream may contain a portion of the ethylene contained in the feedstock. The system may also include a deethanizer for separating the vapor feed stream to recover an overhead stream and a bottoms product stream comprising the $C_{3+}$ hydrocarbons. A refrigerant second stage compression suction drum may be provided for separating the liquid feed stream into a first vapor fraction and a first liquid fraction. A deethanizer overhead condenser allows for cooling and partially condensing the overhead stream via indirect heat exchange with the first liquid fraction, forming a warmed first liquid fraction. A deethanizer reflux drum separates the cooled and partially condensed overhead stream into a liquid reflux stream and an overhead vapor dilute ethylene product stream, and a refrigerant first stage compression suction drum separates the warmed first liquid fraction into a second vapor fraction and a second liquid fraction. A refrigerant compressor may be used for compressing the first vapor fraction and the second vapor fraction to form a compressed refrigerant stream. Also provided are a refrigerant condenser for cooling the compressed refrigerant stream via indirect heat exchange with the second liquid fraction and feeding the second liquid fraction to the deethanizer, and a refrigerant accumulator for separating the cooled compressed refrigerant stream into a third vapor fraction and a third liquid fraction. A flow line may feed the third vapor fraction to the deethanizer, and another flow line may feed the third liquid fraction to the refrigerant second stage compression suction drum.

Other aspects and advantages will be apparent from the following description and the appended claims.

BRIEF DESCRIPTION OF DRAWINGS

FIG. 1 is a simplified process flow diagram of a system for the production of dilute ethylene according to embodiments disclosed herein.

DETAILED DESCRIPTION

In one aspect, embodiments herein relate to processes and systems for recovery of a dilute ethylene stream. More specifically, embodiments disclosed herein relate to processes and systems for separation of a dilute ethylene stream from an offgas or other vapor streams, where the ultra-low temperature refrigeration for the desired separations is provided by the offgas itself, and only moderately-low temperature externally supplied propylene refrigerants (for example, at −40° C. to 15° C.) are necessary.

Ethylene-containing feedstocks useful in embodiments herein may include any number of refinery streams. In various embodiments, the ethylene-containing feedstocks may include an offgas from a fluid catalytic cracker (FCC) unit, residue fluid catalytic cracker (RFCC) unit, and/or a vacuum gas oil (VGO) cracking unit, as well as coker offgas and other refinery streams that may be a mixture of gases including ethylene.

Ethylene-containing feedstocks according to embodiments herein may contain, for example, 0.1 wt % to 60 wt % ethylene, such as from about 5 wt %, 10 wt %, or 13 wt % to about 30 wt %, 40 wt %, or 50 wt % ethylene. The balance of the dilute ethylene stream may include, for example, hydrogen, methane, ethane, propylene, and/or propane. Ethylene-containing feedstocks may also contain various light gases, such as carbon monoxide, carbon dioxide, and/or nitrogen, as well as acetylenes, dienes and heavier hydrocarbons ($C_{4+}$). For example, a typical FCC offgas may include 50 wt % to a 70 wt % methane and hydrogen, with the balance being about equal parts ethane and ethylene, as well as a minor amount of $C_{3+}$ compounds. Various ethylene-containing feedstocks may also include other impurities, such as water, oxygen-containing hydrocarbons, nitrogen-containing hydrocarbons, and mercury, among others.

Referring now to FIG. 1, a simplified process flow diagram of a system for the production of dilute ethylene from various ethylene-containing feedstocks, according to embodiments disclosed herein, is illustrated. An ethylene-containing feedstock 10 may initially be treated to remove some of the impurities, if necessary. For example, the ethylene-containing feedstock 10 may be cooled, such as to a temperature in the range from about 10° C. to about 25° C., to condense water, if present. The cooled ethylene-containing feedstock 11 may then be fed to a feed dryer knock-out drum 16, separating the condensate 18 from the vaporous feedstock 20. The feedstock 20 may then be passed through one or more absorbent beds 22, 24 to remove impurities, such as oxygenates, non-condensed water, and mercury, among other impurities, resulting in a treated feedstock 26.

Following treatment, the ethylene-containing feedstock 26 may be further chilled, condensing at least a portion of the hydrocarbons. Operating conditions should be maintained such that the condensed portion of the hydrocarbons contains some ethylene. The chilled ethylene-containing feedstock 32 may then be separated in a deethanizer feed separator 34, such as in a drum or another type of separator, producing a vapor feed stream 36 and a liquid feed stream 40. The vapor feed stream 36 may contain hydrogen, methane, ethane, and ethylene, as well as some heavier components, such as propylene, propane, and $C_{4+}$ hydrocarbons. The liquid feed stream 40 may contain $C_3$ and heavier hydrocarbons, is partially concentrated in $C_2$s (ethane and ethylene), and may also contain some dissolved lights (methane, hydrogen).

Following separation, the vapor feed stream 36 may be fed to a deethanizer 44. The liquid feed stream 40, concentrated in $C_2$s, is suitable to be fed to a refrigeration loop for providing cooling to the system, as will be described further below.

The components in the vapor feed stream may be separated in deethanizer 44. The deethanizer 44 may be operated under conditions to recover ethane, ethylene and lighter components as an overhead fraction 52, and to recover $C_3$ and heavier components as a bottoms fraction 46. To achieve the desired separations, the deethanizer 44 may be operated at an overheads 52 temperature in the range from about −50° C. to about −35° C., such as in the range from about −42° C. to about −48° C., and at a pressure in the range from about 20 to about 40 bar, such as in the range from about 25 to about 35 bar. The deethanizer 44 may be reboiled, such as by using low pressure steam or other heat transfer media to heat a portion of the bottoms in reboiler 42, and the deethanizer 44 may operate at a bottoms temperature in the range from about 80° C. to about 120° C., such as in the range from about 90° C. to about 100° C.

The bottoms product 46 may be cooled in an exchanger 48 via indirect heat exchange, such as to a temperature in the range from about 25° C. to about 50° C., prior to recovery. The resulting bottoms product 50, which includes $C_3$ and heavier hydrocarbons, may be further processed, such as in an ethylene unit (not shown) to crack the hydrocarbons to produce additional ethylene, or may be utilized as a fuel.

The overhead fraction 52 recovered from the deethanizer 44 may be cooled and partially condensed in exchanger 54, such as to a temperature in the range from about −50° C. to about −65° C., or in the range from about −53° C. to about −59° C. The cooled and partially condensed overhead stream 56 may then be fed to a reflux drum 58, where the overhead stream is separated into a liquid portion 60, which may be used as a reflux fed to the deethanizer 44, and into an overhead vapor product stream 62, the desired dilute ethylene product stream.

The dilute ethylene product stream 62, having a temperature of less than about −50° C., may be used to cool and/or chill the ethylene-containing feedstock 10, which may be provided at a temperature of greater than 30° C. in some embodiments. For example, the dilute ethylene product stream 62 may be first contacted in indirect heat exchange in an exchanger 28 with the treated feedstock 26 (after impurity removal), and may also be contacted in indirect heat exchange in an exchanger 12 with the ethylene-containing feedstock 10, upstream of the feed dryer knock-out drum 16. For example, the ethylene-containing feedstock 10 may be provided at a temperature in the range from about 30° C. to about 50° C., and may be cooled via indirect heat exchange with the dilute ethylene product stream 64, which may be at a temperature in the range from about 0° C. to about 20° C., the ethylene-containing feedstock 10 being cooled to a temperature in the range from about 20° C. to about 25° C. and recovered as stream 13. Upstream of the treaters 22, 24, the ethylene-containing feedstock 13 may also be chilled in an exchanger 14 via indirect heat exchange with a $C_3$ refrigerant, which may be at a temperature in the range from about 5° C. to about 20° C., such as in the range from about 5° C. to about 15° C.

Following treatment, the ethylene-containing feedstock 26, which may be at a temperature in the range from about 0° C. to about 25° C., such as in the range from about 10° C. to about 20° C., may be chilled against the overhead dilute ethylene product stream, which as noted above may be at a temperature of less than −50° C. The ethylene-containing feedstock 26 may also be chilled via indirect heat exchange with a $C_3$ refrigerant, which may be at a temperature in the range from about −30° C. to about −50° C., such as in the range from about −35° C. to about −45° C. In some embodiments, the chilling of the ethylene-containing feedstock may occur in a cold box 28, collectively exchanging the ethylene-containing feedstock 26 against the $C_3$ refrigerant 30 and the dilute ethylene product stream 62. The resulting cooled, treated, chilled, and partially condensed ethylene-containing feedstock 32 may be at a temperature in the range from about −25° C. to about −45° C., such as in the range from about −30° C. to about −40° C., for example.

Refrigeration for the deethanizer overheads condenser 54 may be provided by the liquid feed stream 40 or a portion thereof. The liquid feed stream 40, which may be recovered from the deethanizer feed separator 34 at a temperature in the range from about −25° C. to about −45° C. and a pressure in the range from about 20 to about 40 bar, may be partially expanded, such as to a pressure in the range from about 5 to about 15 bar, reducing the temperature of the liquid feed stream and vaporizing a portion of the lighter components.

Following expansion, the expanded liquid feed stream 74, which may be at a temperature in the range from about −60° C. to about −40° C., may be fed to a second stage refrigerant compressor suction drum 76, where the vaporized portion 78 may be separated from the remaining liquid components 82. The liquid 82 recovered from the second stage suction drum 76 may be further expanded, decreasing the temperature of the stream to a temperature in the range from about −75° C. to about −65° C., such as about −70° C. The expanded liquid 83 may then be contacted in indirect heat exchange with the deethanizer overheads 52, cooling and partially condensing the overheads, as described above, and warming the expanded liquid 83 to a temperature in the range from about −60° C. to about −40° C.

The warmed expanded liquid 84 may be fed to a first stage refrigerant compressor suction drum 86, where the vaporized portion 90 of the expanded liquid may be separated from the remaining liquid components 88. The vaporized portion 90 of the expanded liquid may be fed from the drum to a first stage of a compressor 94, combined with the vapor portion 78 withdrawn from the second stage suction drum 76, and pressurized in a second stage of compressor 94. Compression may result in heating of the refrigerant, recovered via flow line 96, to a temperature in the range from about 60° C. to about 90° C., for example.

The compressed refrigerant 96 may then be cooled, chilled, and partially condensed in one or more heat exchangers. For example, the compressed refrigerant 96 may be fed to exchanger 70 and contacted in indirect heat exchange with the dilute ethylene product stream 66, such as downstream of feed/product interchanger 12, warming the dilute ethylene product stream 64 from a temperature in the range from about 25° C. to about 35° C. to a temperature in the range from about 40° C. to about 50° C. (stream 72), and cooling the compressed refrigerant 96 to a temperature in the range from about 30° C. to about 40° C. The compressed refrigerant 100 may then be further cooled in exchanger 102 via indirect heat exchange with a $C_3$ refrigerant, which may be at a temperature in the range from about 5° C. to about 20° C., such as in the range from about 5° C. to about 15° C.

Further chilling and partial condensation of the resulting compressed refrigerant stream 104 may be performed via indirect heat exchange with the liquid components 88 recovered from the first stage refrigerant compressor suction drum 86. The liquid 88 recovered from the first stage refrigerant compressor suction drum 88, which as noted above may be at a temperature of less than −40° C., may be pumped from the drum and contacted in indirect heat exchange with the compressed refrigerant stream 104. The compressed refrigerant stream 104 may also be chilled and partially condensed via indirect heat exchange with a $C_3$ refrigerant 116, which may be at a temperature in the range from about −30° C. to about −50° C., such as in the range from about −35° C. to about −45° C. In some embodiments, such as illustrated, the chilling of the compressed refrigerant stream 104 may occur in a cold box 106, collectively exchanging the compressed refrigerant stream 104 against the $C_3$ refrigerant 116 and the liquid 88 from the first stage refrigerant compressor suction drum 86. The resulting compressed, cooled, treated, chilled, and partially condensed refrigerant 108 may be at a temperature in the range from about −5° C. to about −35° C., such as in the range from about −15° C. to about −25° C., for example, and at a pressure in the range from about 25 to about 35 bar.

The refrigerant 108 may then be fed to a refrigerant accumulator drum 110, separating a condensed portion 114 of the refrigerant from a non-condensed portion 112 of the refrigerant. The condensed portion 114 of the refrigerant may be combined with the liquid feed 40 from the deethanizer feed separator 34 and routed to the refrigerant compressor suction drum 76.

The non-condensed portion 112 of the refrigerant may be fed to the deethanizer column 44 for recovery of the hydrocarbons, including any ethane and ethylene present. The liquid recovered from the first stage refrigerant compressor suction drum, recovered as stream 115 following exchange with the compressed refrigerant, may also be fed to the deethanizer 44 for recovery of the hydrocarbons. In this manner, the lights are purged from the refrigeration loop as the total non-condensables from the refrigerant accumulator drum 110 and sent to an upper section of the deethanizer 44 for full recovery, and the heavies are purged from the refrigeration loop as a portion 115 of the condensed refrigerant 114 from the refrigerant accumulator 110. This heavy blowdown is also used to provide some auto-refrigeration to the refrigerant condenser 106 and in doing so is pre-heated before being fed to a lower section of the deethanizer 44 for full recovery.

As described above, the separations are highly integrated, the ethylene-containing feedstock itself being used to provide refrigeration for the desired separations. Process control may be effected in a number of manners. In some embodiments, control of the overhead pressure of the deethanizer column 44 may be effected by controlling a flow rate of the dilute ethylene product stream 66, where the flow rate is controlled downstream of both the feed cooler 12 and the deethanizer feed chiller 28.

The resulting dilute ethylene product stream 66 may be used as a feed to one or more downstream processes. In some embodiments, at least a portion 72 of the overhead vapor dilute ethylene product stream 66 may be fed to a downstream reaction zone (not illustrated), where the ethylene may be used as a reactant. For example, the dilute ethylene product may be fed an alkylation reaction zone, such as for the conversion of benzene to ethylbenzene. Additionally or alternatively, at least a portion 68 of the overhead vapor dilute ethylene product stream may be fed to a combustion system (not illustrated) as a fuel gas Control of the reflux drum 58 temperature may be effected by controlling or indirectly controlling a refrigerant compressor 94 output pressure in various embodiments. For example, the deethanizer 44 overhead condensing temperature, as measured in the reflux drum 58, may be controlled by manipulating the speed of the refrigerant compressor 94. The deethanizer 44 pressure may be controlled by throttling the dilute ethylene product flow leaving the unit. The refrigerant compressor first stage suction drum 86 pressure may be controlled by throttling the flow to the first stage of the compressor. The refrigerant compressor second stage suction drum 76 pressure may be controlled by throttling the lights purge to the flare. The refrigerant compressor 94 discharge pressure, while not directly controlled, may be a result of the compressor performance curve based on the controlled suction pressure and the compressor speed, resulting from the deethanizer 44 overhead condensing temperature controller.

Although the non-condensables in the refrigerant may be forwarded to the deethanizer 44 for full recovery, it may still be desired to purge a portion of the refrigerant from the refrigeration loop. For example, a portion 92, 80 of the vapor fractions 90, 78, from one or both of the compressor suction drums 86, 76, respectively, may be withdrawn as a purge.

As noted above, $C_3$ refrigerant may be used as a heat sink in various portions of the process. Systems according to embodiments herein may include, for example, a closed-loop $C_3$ refrigeration system for providing the $C_3$ refrigerant at two or more temperature levels, such as those ranges noted above.

As described above, FCC, RFCC and/or VGO offgases can be utilized as a less expensive source of ethylene for various processes. These dilute ethylene gases must be pretreated to remove impurities that are harmful to downstream catalysts. Various degrees of cryogenic separation are then necessary to remove other undesirable hydrocarbons, such as heavier olefins and non-olefins (e.g., propylene, propane and C4s). The cryogenic fractionation typically requires a very low level of refrigeration.

FCC, RFCC and/or VGO offgases may be first pretreated by an amines and/or caustic wash as a first step in removing acid gases. The scrubbed gas may then be sent to an oxygen converter for conversion of oxygen and oxygenated compounds to water. Oxygen-free gas may then be sent to a second stage amines and/or caustic scrubber as a polishing step in acid gas removal. The scrubbed gas may then be compressed, chilled and dried to facilitate cryogenic distillation. A mercury absorber may also be utilized to protect downstream exchangers, such as brazed aluminum exchangers.

The resulting treated and compressed feed gas, which may be at a temperature of about 40° C. may be cooled against product gas, which may be at a temperature of about 10° C., in the $C_2$ feed/product exchanger. Cooled feed gas, which may be at a temperature of about 22° C., may then be chilled against $C_3$ refrigerant in the dryer feed chiller and dried in the feed dryer. Chilled and dried feed gas, which may be at a temperature of about 15° C., may then be sent to the deethanizer feed chiller, where it is chilled against very cold product gas, which may be at a temperature of about −56° C. in a braised aluminum exchanger. $C_3$ refrigerant may be utilized as an additional heat sink and for temperature control in the chiller.

Chilled feed gas, which may be at a temperature of about −35° C., may then be sent to the deethanizer feed separator, where condensed liquid is separated from non-condensed vapor. The vapor fraction is then fed to the deethanizer and the liquid fraction is used as make-up to an integral $C_2$ refrigeration system. In the deethanizer, hydrogen, methane, ethylene, and ethane are recovered as overhead vapor distillate while propylene, propane and heavier components are recovered as bottoms product.

The Deethanizer overhead is partly condensed by $C_2$ refrigerant and the condensate is used as reflux to the column. The uncondensed overhead, including ethylene, ethane and lights (i.e., hydrogen and methane) is the product gas, which may be fed to a downstream reactor, such as an EB Unit. Cold product gas from the deethanizer reflux drum, which may be at a temperature of about −56° C., is heated against cooled feed gas, which may be at a temperature of about 15° C., to a temperature of about 10° C. in the previously mentioned deethanizer feed chiller, then further heated against hot feed gas, which may be at a temperature of about 40° C., to a temperature of about 30° C., and finally heated against $C_2$ refrigerant compressor discharge, which may be at a temperature of about 76° C., in the $C_2$ refrigerant cooler to a temperature of about 45° C., for example, before being sent to the downstream reaction zone. The propylene and heavier bottoms of the deethanizer, which may be at a temperature of about 100° C., may be cooled against cooling water and sent to an ethylene unit for hydrocarbon recovery, or utilized as fuel.

The integral $C_2$ refrigeration system includes a first stage suction drum with pump, a 2-stage refrigerant compressor, a second stage suction drum, a $C_2$ refrigerant cooler, a $C_2$ refrigerant chiller, a $C_2$ refrigerant condenser and a $C_2$ refrigerant accumulator. The integral $C_2$ refrigeration system produces refrigerant at two temperature levels, such as −56° C. and −60° C. Refrigerant from the second stage suction drum is flashed into the cold side of the deethanizer condenser, which may be a braised aluminum exchanger, where the $C_2$ refrigerant flashes from −47° C. down to −70° C., and then boils from −70° C. to −50° C. This cooling curve provides sufficient gradient for the condensing deethanizer overhead, which condenses from −46° C. to −56° C. in the hot side of the deethanizer condenser.

Condensed liquid from the deethanizer feed separator is sent to the second stage suction drum as make-up to the integral $C_2$ refrigeration system. This stream is partially concentrated in $C_2$s, but still contains some lights, $C_3$s and heavies. The lights are purged from the refrigeration loop as the total non-condensables from the $C_2$ refrigerant accumulator and sent to the upper section of the deethanizer for full recovery. The heavies are purged from the refrigeration loop as a portion of the condensed refrigerant from the $C_2$ refrigeration accumulator. This heavy blowdown is also used to provide some auto-refrigeration to the $C_2$ refrigerant condenser and in doing so is pre-heated before being fed to the lower section of the deethanizer for full recovery.

Non-vaporized refrigerant from the first stage suction drum, which constitutes a portion of the refrigerant heavies purge, is also sent to the deethanizer. This heavy purge is also used to provide some cooling to the $C_2$ refrigerant condenser and in doing so is pre-heated before being fed to the lower section of the deethanizer for full recovery of hydrocarbons.

The integral $C_2$ refrigeration system used in embodiments herein requires no externally supplied source of ethylene refrigerant. The process heat sink is provided by a closed loop $C_3$ refrigeration system operating at two refrigerant temperature levels, such as 12° C. and −40° C. Utility requirements are the electrical power to the $C_2$ refrigerant compressor and the $C_3$ refrigeration package.

As described above, A process for the production of a dilute ethylene feedstock by cryogenic separation of $C_3$s and heavier components from the offgas of a FCC, RFCC and/or VGO unit, without the need for an externally supplied low temperature ethylene or binary refrigerant, is described. In embodiments herein, propane or propylene refrigerant is the lowest temperature level of refrigeration that is required. FCC offgas is separated into a dilute ethylene product stream containing ethylene, ethane, methane, hydrogen and other light components and a stream containing propane, propylene, $C_4$s, $C_5$s and heavier components in a deethanizer.

The deethanizer, which may operate at a pressure of about 30 bar, which may be required when located upstream of an EB unit using the produced dilute ethylene product stream, may have an overhead temperature of approximately −46 to −56° C. Condensing at this temperature cannot be performed with propane or propylene refrigeration, and typically requires ethylene or ethylene/propylene binary refrigeration. Embodiments disclosed herein avoid the need for an external ethylene or binary refrigerant.

After the usual pre-treatment and drying, FCC offgas feed is chilled in order to produce a mixed $C_2/C_3$ stream that is used as make-up refrigerant to the integral $C_2$ refrigeration system. A continuous heavies blowdown and lights purge are taken from the refrigeration system to maintain a usable steady-state composition of refrigerant. Refrigeration system blowdown and purge are returned to the deethanizer for complete product and by-product recovery. Extensive heat integration may be utilized to recoup heat and minimize cooling. The integral $C_2$ refrigeration system rides off of the deethanizer pressure. The resultant dilute ethylene product gas is suitable as feedstock to an ethylbenzene unit. The byproduct $C_3$+ stream can be recycled to an ethylene unit or burned as fuel.

Prior practice was to utilize separate ethylene and propylene refrigeration systems or a binary ethylene/propylene refrigeration system to provide low-temperature refrigerant for condensing Deethanizer overhead. These refrigeration systems needed to be charged with high-purity ethylene and high-purity propylene. Embodiments herein utilize feed gas as the sole source of make-up refrigerant to the $C_2$ refrigeration system. It was unexpected that the composition of the condensed feed gas (after initial chilling) would be suitable for use as a refrigerant for the deethanizer condenser. The vaporization curve of the resulting $C_2$ refrigerant, however, matches the condensing curve of the Deethanizer overhead. This match of feed-based refrigerant to deethanizer overhead condensing has been found to be valid over a wide range of dilute ethylene feed compositions that are typical of FCC, RFCC and VGO offgases.

It was also unexpected that the $C_2$ refrigeration system could be started up by using only a small amount of $C_3$ refrigeration to "boot-strap" the integral $C_2$ refrigeration system. It was unexpected that a large portion of the steady-state net heat removal could be recovered by product gas and to a lesser extent by the $C_3$ refrigerant. The heat contained in the hot product gas may also be fully recovered in a downstream EB unit.

It was also unexpected that the open loop refrigeration cycle could also serve to help separate the lights from the dilute $C_2$ product gas and the $C_3$s and heavies from the dilute $C_2$ product gas. This is accomplished via the two-stage refrigerant flash and the lights vent and heavies blowdown, which are fed to the top and bottoms sections of the deethanizer, respectively. The lights purge is taken as the non-condensable vent from the $C_2$ refrigerant accumulator, which is the lightest stream in the mixed $C_2$ refrigeration system. The heavies purge is taken from the first stage suction drum, which is the heaviest stream in the mixed $C_2$ refrigeration system. The lights and heavies separation that occurs in the refrigeration system serves to reduce the load on the deethanizer.

Advantageously, embodiments disclosed herein eliminate the need for an ethylene or ethylene/propylene (binary) refrigerant to condense the deethanizer overheads. A primary advantage of embodiments herein is the elimination of a more expensive external closed loop ethylene or binary refrigeration system. Another advantage is the elimination of the need for an external source of high-purity ethylene, which may or may not be available at the plant site, as refrigerant make-up. If make-up ethylene must be trucked in, it would represent a very high cost and operational difficulty. During prolonged shutdowns, the ethylene will vaporize and must be vented to flare since it is not possible to contain ethylene at ambient temperatures. The need for high-purity ethylene make-up complicates startups and adds very high costs to initial operations. Embodiments herein provide a clear low-cost alternative to Low Pressure Ethylene Recovery (LPR) with a binary refrigerant, as well as ease of start-up.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed is:

1. A system for producing a dilute ethylene stream, the system comprising:
   a deethanizer feed chiller for cooling and partially condensing a feedstock comprising hydrogen, methane, ethane, ethylene, and $C_{3+}$ hydrocarbons;
   a deethanizer feed separator for separating the cooled and partially condensed feedstock into a vapor feed stream and a liquid feed stream, wherein the liquid feed stream comprises a portion of the ethylene contained in the feedstock;
   a deethanizer for separating the vapor feed stream to recover an overhead stream and a bottoms product stream comprising the $C_{3+}$ hydrocarbons;
   a refrigerant drum for separating the liquid feed stream into a first vapor fraction and a first liquid fraction;
   a deethanizer overhead condenser for cooling and partially condensing the overhead stream via indirect heat exchange with a refrigerant comprising the first liquid fraction;
   a refrigerant first stage compression suction drum for separating the first liquid fraction into a second vapor fraction and a second liquid fraction;
   a refrigerant compressor for compressing the first vapor fraction and the second vapor fraction to form a compressed refrigerant stream;

a refrigerant condenser for cooling the compressed refrigerant stream via indirect heat exchange with the second liquid fraction and feeding the second liquid fraction to the deethanizer.

2. The system of claim 1, further comprising a deethanizer reflux drum for separating the cooled and partially condensed overhead stream into a liquid reflux stream and an overhead vapor dilute ethylene product stream.

3. The system of claim 1, further comprising a refrigerant accumulator for separating the cooled compressed refrigerant stream into a third vapor fraction and a third liquid fraction.

4. A system for producing a dilute ethylene stream, the system comprising:
   a deethanizer feed chiller for cooling and partially condensing a feedstock comprising hydrogen, methane, ethane, ethylene, and $C_{3+}$ hydrocarbons;
   a deethanizer feed separator for separating the cooled and partially condensed feedstock into a vapor feed stream and a liquid feed stream, wherein the liquid feed stream comprises a portion of the ethylene contained in the feedstock;
   a deethanizer for separating the vapor feed stream to recover an overhead stream and a bottoms product stream comprising the $C_{3+}$ hydrocarbons;
   a refrigerant second stage compression suction drum for separating the liquid feed stream into a first vapor fraction and a first liquid fraction;
   a deethanizer overhead condenser for cooling and partially condensing the overhead stream via indirect heat exchange with the first liquid fraction, forming a warmed first liquid fraction;
   a deethanizer reflux drum for separating the cooled and partially condensed overhead stream into a liquid reflux stream and an overhead vapor dilute ethylene product stream;
   a refrigerant first stage compression suction drum for separating the warmed first liquid fraction into a second vapor fraction and a second liquid fraction;
   a refrigerant compressor for compressing the first vapor fraction and the second vapor fraction to form a compressed refrigerant stream;
   a refrigerant condenser for cooling the compressed refrigerant stream via indirect heat exchange with the second liquid fraction and feeding the second liquid fraction to the deethanizer;
   a refrigerant accumulator for separating the cooled compressed refrigerant stream into a third vapor fraction and a third liquid fraction;
   a flow line for feeding the third vapor fraction to the deethanizer;
   a flow line for feeding the third liquid fraction to the refrigerant second stage compression suction drum.

5. The system of claim 4, further comprising:
   one or more heat exchangers for cooling a feed gas;
   a feed dryer knock-out drum for removing condensates from the feed gas;
   one or more feed treaters for removing impurities from the feed gas, producing the feedstock.

6. The system of claim 5, wherein the contaminants comprise one or more of water, oxygen-containing hydrocarbons, nitrogen-containing hydrocarbons, or mercury.

7. The system of claim 5, wherein the one or more exchangers for cooling the feed gas comprise:
   a heat exchanger configured to exchange heat between the feed gas and the dilute ethylene product stream; and
   a second heat exchanger configured to exchange heat between the feed gas and a $C_3$ refrigerant stream.

8. The system of claim 4, wherein the deethanizer feed chiller comprises a cold box configured to exchange heat between the feedstock, the dilute ethylene product stream, and a $C_3$ refrigerant stream.

9. The system of claim 4, wherein the refrigerant condenser comprises a cold box configured to exchange heat between the compressed refrigerant stream, the second liquid fraction, and a $C_3$ refrigerant stream.

* * * * *